(12) United States Patent
Brown

(10) Patent No.: US 11,771,065 B2
(45) Date of Patent: Oct. 3, 2023

(54) FORMULATIONS AND METHODS FOR PROMOTING HONEYBEE HEALTH

(71) Applicant: API HOLDINGS, LLC, Merced, CA (US)

(72) Inventor: Justin Jay Brown, Atwater, CA (US)

(73) Assignee: API HOLDINGS, LLC, Merced, CA (US)

( * ) Notice: Subject to any disclaimer, the term of this patent is extended or adjusted under 35 U.S.C. 154(b) by 0 days.

(21) Appl. No.: 15/753,899

(22) PCT Filed: Aug. 18, 2016

(86) PCT No.: PCT/US2016/047645
§ 371 (c)(1),
(2) Date: Feb. 20, 2018

(87) PCT Pub. No.: WO2017/031371
PCT Pub. Date: Feb. 23, 2017

(65) Prior Publication Data
US 2018/0235191 A1  Aug. 23, 2018

Related U.S. Application Data

(60) Provisional application No. 62/207,523, filed on Aug. 20, 2015.

(51) Int. Cl.
| | | |
|---|---|---|
| *A01K 51/00* | (2006.01) | |
| *A01N 63/22* | (2020.01) | |
| *A61K 31/538* | (2006.01) | |
| *A61K 35/742* | (2015.01) | |
| *A61K 47/02* | (2006.01) | |
| *A61K 47/12* | (2006.01) | |

(52) U.S. Cl.
CPC .............. *A01K 51/00* (2013.01); *A01N 63/22* (2020.01); *A61K 31/538* (2013.01); *A61K 35/742* (2013.01); *A61K 47/02* (2013.01); *A61K 47/12* (2013.01)

(58) Field of Classification Search
CPC ...... A01K 51/00; A01K 53/00; A61K 31/538; A61K 35/742; A61K 47/02; A61K 47/12
USPC ..................................... 449/1–3, 9
See application file for complete search history.

(56) References Cited

U.S. PATENT DOCUMENTS

| | | | | |
|---|---|---|---|---|
| 6,096,350 A | * | 8/2000 | Kemp | A01N 59/00 424/661 |
| 2002/0034529 A1 | * | 3/2002 | Prince | A01K 51/00 424/405 |
| 2006/0009122 A1 | * | 1/2006 | Swanson | A01N 37/02 449/2 |
| 2006/0148378 A1 | * | 7/2006 | Cohen | A01K 53/00 449/2 |
| 2013/0136695 A1 | * | 5/2013 | Hargis | A61K 35/742 424/9.2 |
| 2014/0045407 A1 | | 2/2014 | Van Hoorn et al. | |
| 2015/0216203 A1 | * | 8/2015 | Isaksen | A61K 35/742 424/93.45 |
| 2015/0216871 A1 | * | 8/2015 | Kuhnert | A61K 31/538 514/229.8 |

FOREIGN PATENT DOCUMENTS

| | | | | |
|---|---|---|---|---|
| DE | 3515851 A1 | * | 11/1986 | ............. A01K 51/00 |
| DE | 4215534 C1 | | 6/1993 | |
| FR | 2985664 B1 | * | 8/2014 | ............. A01K 51/00 |

OTHER PUBLICATIONS

English-language translation of DE 4215534 (Year: 1993).*
English-language translation of FR 2985664 (Year: 2013).*
International Search Report; International Application No. PCT/US2016/047645; dated Nov. 3, 2016.
https://www.youtube.com/watch?v=w64NeenUNPE; 2016. Transcript with video capture for full context, Examiner is invited to watch the link above.

* cited by examiner

*Primary Examiner* — Brian Gangle
*Assistant Examiner* — Lakia J Jackson-Tongue
(74) *Attorney, Agent, or Firm* — Knobbe, Martens, Olson & Bear LLP

(57) ABSTRACT

Formulations for promoting honeybee health include an aqueous solution having an organic acid, one or more buffering agents, one or more coloring dyes, and one or more strains of probiotic bacteria. The formulations can be in the form of syrup additives or sprays. The formulations can have additional active ingredients, inert ingredients, or both.

14 Claims, No Drawings

US 11,771,065 B2

FORMULATIONS AND METHODS FOR PROMOTING HONEYBEE HEALTH

RELATED APPLICATIONS

This application if the U.S. National Phase entry application under 35 U.S.C. § 371 of PCT/US2016/047645, filed on Aug. 18, 2016, which is a non-provisional application that claims priority to U.S. Provisional Application No. 62/207,523 filed on Aug. 20, 2015; the entire disclosure of which is incorporated herein.

BACKGROUND

Disclosed herein are safe, effective and economical formulas and related methods for improving the health of honeybees and more particularly for treating the most common honeybee pathogens, including fungal, bacterial and viral pathogens.

Nosema apis is a microsporidian, a small, unicellular parasite recently reclassified as a fungus that mainly affects honey bees. It causes nosemosis, also called Nosema, which is the most common and widespread of adult honeybee diseases. The dormant stage of N. apis is a long-lived spore which is resistant to temperature extremes and dehydration, and cannot be killed by freezing the contaminated comb. The symptoms of Nosema are relatively nonspecific, which makes it difficult to distinguish from other diseases of the honeybee. It arises mostly in the spring after periods of bad weather, although it may also be a winter disease that is only noticed in the spring when beekeepers first inspect their hives. The female worker bees are most strongly afflicted, less so the drones. The queen bee is rarely infected since afflicted bees rarely participate in feeding the queen. The most notable symptom is dysentery. This appears as yellow stripes on the outside of the hive and in severe cases, inside the hive. Bees may be unable to fly ("crawling") due to disjointed wings.

Treatment with the antibiotic Fumagilin-B (prepared from Aspergillus fumigatus, the causative agent of stonebrood), interrupts the vegetative state of the N. apis, but does not affect the spores themselves. This is the oldest known product for Nosema being on the market for more than 60 years. Fumagilin-B is reported to cause birth defects in mammals. In addition, Fumagilin-B may kill the normal "healthy" bacterial flora of the honeybee. Because Fumagilin-B does not kill the spores, disinfection of the honeycombs and utensils is recommended for an extensive disease outbreak. The spores are sensitive to chemicals such as acetic acid and formaldehyde, and physical radiation: ultrasonic and gamma radiation. Heat treatment in 49° C. (120° F.) for 24 hours can be used to kill the spores on contaminated equipment.

More holistic products, such as NOZEVIT and OPTIMA COMPLETE, have also been marketed for treatment of Nosema. These products are made by the same company and contain an amalgamation of oak tree tannins, 14 essential oils, vitamins, minerals and amino acids, it is said that this product due to its make-up causes the gut bacteria of the bee to flourish at a more effective rate, thus making it more difficult for the N. apis to take hold within the bee. Cost varies upon quantity but can be as much as $800.00 for a 5 gallon tube that will treat 5 totes of 250 gallon of syrup.

American foulbrood is caused by the rod-shaped, spore-forming bacteria, Paenibacillus larvae. P larvae infection is the most widespread and destructive of the bee brood diseases. Bee larvae up to 3 days old become infected by ingesting spores that are present in their food. Young larvae less than 24 hours old are most susceptible to infection. Spores germinate in the gut of the larva and the vegetative form of the bacteria begins to grow, taking its nourishment from the larva. Spores will not germinate in larvae over 3 days old. Infected larvae normally die after their cell is sealed. The vegetative form of the bacterium will die but not before it produces many millions of spores. Each dead larva may contain as many as 100 million spores. This disease only affects the bee larvae but is highly infectious and deadly to bee brood. Infected larvae darken and die.

Various antibiotics and antimicrobial products are available for treating American foulbrood. Antibiotics, in non-resistant strains of the pathogen, can prevent the vegetative state of the bacterium forming. Drug treatment to prevent the American foulbrood spores from successfully germinating and proliferating is possible using, e.g., oxytetracycline hydrochloride (Terramycin) and tylosin tartrate. Unfortunaltely, such broad spectrum antibiotics kill beneficial bacteria as well as P larvae. Moreover, the pathogenic bacterial can build a tolerance to such antibiotics.

Other products on the market for American foulbrood include SUPER BEE DFM, a probiotic formulation that contains a variety of mixed fungus and bacteria, which are designed to compete with pathogenic strains, like P larvae. HIVE ALIVE is another probiotic formulation that contains bacteria, which will compete with infectious strains. More particularly, SUPER BEE DFM includes dried Lactobacillus acidophilus fermentation product, dried Enterococcus faecium fermentation product, dried Bifidobacterium bifidum fermentation product, dried Lactobacilus plantarum fermentation product, dried Saccharomyces cerevisiae fermentation product, dried Bacillus subtilus fermentation product, dried Bacillus lichenformis fermentation product, dried Bacillus pumilus fermentation product, dried Trichoderma longibrachiatrum fermentation extract, and dried Bacillus subtilus fermentation extract. HIVE ALIVE includes thymol, lemon grass and a Macro algae extract.

Bee products are also available for treatment of viral pathogens. These include HONEY "B" HEALTHY, which is made from lemon grass and spearmint oils, this product claims to destroy the protein capsules of the virus. Similarly, PRO HEALTH (from Mann Lakes) claims to have antiviral efficacy. It contains lemon grass and spearmint oils, but also adds thymol oils.

Varroa is a genus of parasitic mites associated with honey bees. Varroa mites are recognised as one of the biggest pests to honeybees worldwide, and may be the single largest contributing factor in the modern-day decline of honeybees, due mainly to their tendency to transmit viral diseases to larval or pupating bees, potentially resulting in colony collapse. Mite populations are typically higher in Autumn.

Most of the products available for treating honeybee pathogens treat only specific pathogens, e.g., N. apis (nosema) and P. larvae (American foulbrood). Further, even those products available for promoting general heath of honeybees lack sufficient efficacy. Accordingly, a need remains for a formulation that broadly targets the most common honeybee diseases, including Nosema, American foulbreed, Varroa mites, viral infections, and also promotes general health and vitality of honeybees.

SUMMARY

A formulation is disclosed for promoting honeybee health. The formulation includes an aqueous solution comprising an organic acid, one or more buffering agents, one or more coloring dyes, and one or more strains of probiotic bacteria. In certain embodiments, the disclosed formulation does not include antibiotics, anti-microbial agents, anti-fungal agents, yeast, fungal metabolites or fungal extracts. In other embodiments, the formulation is free of Fumagilin-B, oxytetracycline hydrochloride (Terramycin), tylosin tartrate, dried *Saccharomyces cerevisiae* fermentation product or *Trichoderma longibrachiatrum* fermentation extract.

In one embodiment, the organic acid is selected from the group consisting of humic acid, fulvic acid, citric acid, gallic acid and malic acid. In one particular embodiment, the organic acid is humic acid. The humic acid maybe present in an amount from about 0.1 to about 10 Kg humic acid per 10 liters total volume. In another embodiment, the humic acid is present in an amount of about 1.134 Kg humic acid per 10 liters total volume.

The one or more buffering agents may be selected from the group consisting of citric acid and sodium bicarbonate. In some embodiments, the aqueous solution comprises about 4 grams of citric acid and about 4 grams of sodium bicarbonate per 10 liters total volume.

The one or more coloring dyes may be selected from the group consisting of brilliant blue and lemon yellow. In some embodiments, the aqueous solution comprises about 0.16 grams of brilliant blue and about 0.16 grams of lemon yellow per 10 liters total volume.

The one or more strains of probiotic bacteria may be selected from the group consisting of *Bacillus subtilis, Bacillus pumilus, Bacillus licheniformis, Bacillus megaterium,* and *Bacillus laterosporus.* In other embodiments, additional bacteria may be selected from *Lactobacillus acidophilus, Enterococcus faecium, Bifidobacterium bifidum,* and *Lactobacilus plantarum.* In some embodiments, the aqueous solution comprises about 0.064 grams of each dried *bacillus* culture per 10 liters total volume.

The formulation may be in the form of a syrup additive or a spray.

In some embodiments, the formulation may include additional ingredients selected from vitamins, co-factors, minerals, essential oils, micronutrients, sugars, gelatin or other gelling agents. Other added ingredients may include conventional bee antibiotics and antifungals, including without limitation, oxytetracycline, tylosin tartrate, lincomycin hydrochloride, terramycin, fluvalinate, fumagillin, and combinations of these and other known antibiotic/antifungals.

In one embodiment, the organic acid in the formulation is fulvic acid and the formulation further includes nitrogen, phosphate, potassium, calcium, including salts thereof, and one or more amino acids selected from the group consisting of alanine, arginine, aspartic acid, glutamic acid, glycine, histidine, isoleucine, lysine, phenylalanine, proline, serine, threonine, valine, and tyrosine.

A kit is disclosed for making the above-described formulation. The kit comprises humic acid, citric acid and sodium bicarbonate, brilliant blue and lemon yellow dyes, and a dried probiotic culture mix, comprising *Bacillus subtilis, Bacillus pumilus, Bacillus licheniformis, Bacillus megaterium,* and *Bacillus laterosporus.* In some embodiments, the ingredients of the kit are pre-weighed and packaged in sterile disposable bags sufficient for mixing 10 liters of formulation. In some embodiments, the kit also includes instructions for mixing, activating and using the formulation.

A method of treating and/or preventing a honeybee infection is also disclosed. The method includes mixing the above-described formulation and administering the formulation to a honeybee colony in need thereof. The administering step may include feeding the formulation in a 1:1 to 1:2 mixture of formulation to standard beekeepers sugar syrup. Alternatively or in addition, the administering step may include spraying the formulation directly onto a brood nest of the colony.

DETAILED DESCRIPTION

Various formulations comprising dilute organic acids supplemented with buffering agents, color dyes and one or more strains of probiotic bacteria are disclosed for promoting health in honeybee colonies. The formulations disclosed include APICARE™ SYRUP ADDITIVE designed to supplement conventional beekeepers sugar syrup, APICARE™ SPRAY designed for direct spray application for the main brood nest of the colony, and SUNSHINE™ SPRAY, which is clear and less likely to contribute color to the honey. The specific syrup and spray formulations have been found to provide surprising health benefits to honeybee colonies, including treatment of the most common honeybee parasites and infections (including e.g., *Varroa* mites, *Nosema,* American foulbrood, as well as viral infections). Methods are also disclosed for feeding and applying the APICARE and SUNSHINE formulations to bee colonies in need thereof.

APICARE™ Syrup Additive

APICARE Syrup additive is made by first mixing an organic acid with water to form a vehicle. One preferred organic acid is humic acid, including e.g., its lower molecular weight constituent, fulvic acid. Other organic acids contemplated for use in APICARE syrup include citric acid, malic acid or gallic acid. Humic acid is a principal component of humic substances, which are the major organic constituents of soil (humus), peat, coal, many upland streams, dystrophic lakes, and ocean water. It is produced by biodegradation of dead organic matter. It is not a single acid; rather, it is a complex mixture of many different acids containing carboxyl and phenolate groups so that the mixture behaves functionally as a dibasic acid or, occasionally, as a tribasic acid. Humic acids can form complexes with ions that are commonly found in the environment creating humic colloids. Humic and fulvic acids (fulvic acids are humic acids of lower molecular weight and higher oxygen content than other humic acids) are commonly used as a soil supplement in agriculture, and less commonly as a human nutritional supplement. As a nutrition supplement, fulvic acid can be found in a liquid form as a component of mineral colloids. Fulvic acids are poly-electrolytes and are unique colloids that diffuse easily through membranes whereas all other colloids do not.

Citric acid is a weak organic acid with the formula $C_6H_8O_7$. It is a natural preservative which is present in citrus fruits. It is also used to add an acidic or sour taste to foods and drinks. In biochemistry, the conjugate base of citric acid, citrate, is important as an intermediate in the citric acid cycle, which occurs in the metabolism of all aerobic organisms. It consists of 3 carboxyl (R—COOH) groups. Citric acid is a commodity chemical, and more than a million tons are produced every year by fermentation. It is used mainly as an acidifier, as a flavoring, and as a chelating agent. Citric acid exists in greater than trace amounts in a variety of fruits and vegetables, most notably citrus fruits. Lemons and limes have particularly high concentrations of the acid; it can constitute as much as 8% of the dry weight of these fruits (about 47 g/L in the juices).

Gallic acid is a trihydroxybenzoic acid, a type of phenolic acid, a type of organic acid, also known as 3,4,5-trihydroxybenzoic acid, found in gallnuts, sumac, witch hazel, tea leaves, oak bark, and other plants. The chemical formula is $C_6H_2(OH)_3COOH$. Gallic acid is found both free and as part of hydrolyzable tannins.

Malic acid is an organic compound with the molecular formula $C_4H_6O_5$. It is a dicarboxylic acid that is made by all living organisms, contributes to the pleasantly sour taste of fruits, and is used as a food additive. Malic acid contributes to the sourness of green apples. It is present in grapes and in most wines with concentrations sometimes as high as 5 g/l. It confers a tart taste to wine, although the amount decreases with increasing fruit ripeness. The taste of malic acid is very clear and pure in rhubarb, a plant for which it is the primary flavor.

In one embodiment, the vehicle of APICARE Syrup additive is made by mixing from about 0.1 to about 10 Kg, from about 0.5 to about 5 Kg, from about 0.8 to about 3 Kg, from about 0.9 to about 2 Kg, or about 1 Kg of humic acid with distilled and/or reverse osmosis filtered water to a total volume of about 10 liters. In one embodiment, about 1.134 Kg humic acid is mixed with 9.462 liter of distilled and/or reverse osmosis filtered water. The diluted humic acid vehicle is blended for about 30-60 minutes in a sterile container at room temperature, or until the solution is clear. In one embodiment, the humic acid may have the chemical formula: $C_{187}H_{186}O_{89}N_9S_1$.

Next, buffers and/or preservatives may be added to the organic acid vehicle. Colored dyes may also be added. Probiotic bacteria may also be included. In one embodiment, a humic acid vehicle is supplemented with one of more of the following ingredients: citric acid (or sodium citrate), sodium bicarbonate, brilliant blue dye, lemon yellow dye, *Bacillus subtilis, Bacillus pumilus, Bacillus licheniformis, Bacillus megaterium,* and *Bacillus laterosporus.* Of course, other probiotic and/or beneficial bacteria may be added. Additional ingredients may also include vitamins, co-factors, minerals, essential oils, micronutrients, sugars, gelatin or other gelling agents, etc. In one embodiment, the syrup includes 4 grams of citric acid and 3.936 grams of sodium bicarbonate, 0.16 grams of brilliant blue and 0.16 grams of lemon yellow, 0.064 grams of *Bacillus subtilis,* 0.064 grams of *Bacillus pumilus,* 0.064 grams of *Bacillus licheniformis,* 0.064 grams of *Bacillus megaterium,* and 0.064 grams of *Bacillus laterosporus.* These additives may be added in dry form about 2, 4, 6, 8, 10, 12, 18, 24, 36 or 72 hours before use to allow a homogeneous and activated syrup additive. The probiotic bacteria hydrate and become active. Preferably, the APICARE Syrup additive is made about 24 hours before use to allow optimal mixing and culture activation.

In another combination, the formula may include in addition to humic acid and the other ingredients, one or more, two or more, three or more, four or more probiotic bacteria—selected from *Bacillus subtilis, Bacillus pumilus, Bacillus licheniformis, Bacillus megaterium, Bacillus laterosporus, Bifidobacterium* species and *Lactobacillus* species.

APICARE™ Spray

APICARE Spray has the same components as the syrup additive, but is formulated to have a sprayable viscosity. In one embodiment, the organic acid vehicle for the spray is made by mixing about 0.085 Kg of humic acid in about 9.462 liters of distilled and/or reverse osmosis filtered water. In one embodiment, the spray includes 4 grams of citric acid and 3.936 grams of sodium bicarbonate, 0.16 grams of brilliant blue and 0.16 grams of lemon yellow, 0.064 grams of *Bacillus subtilis,* 0.064 grams of *Bacillus pumilus,* 0.064 grams of *Bacillus licheniformis,* 0.064 grams of *Bacillus megaterium,* and 0.064 grams of *Bacillus laterosporus.* Preferably, the homogeneous, activated spray is made about 24 hours before use. As detailed above for the syrup, other organic acids may be substituted for humic acid. Likewise, the spray formulation may include any one or more of the additives, or other ingredients disclosed. Other beneficial bacteria may also be used.

SUNSHINE™ Spray

SUNSHINE Spray is formulated to be a clear sprayable liquid. In one embodiment, the organic acid vehicle for the spray is fulvic acid ($C_{135}H_{182}O_{95}N_5S_2$). The fulvic acid vehicle may include about 1% to about 10% fulvic acid (v/v in purified water). In various embodiments, the fulvic acid may be diluted to 1%, 2%, 3%, 4%, 5%, 6%, 7%, 8%, 9% or 10% in purified water. In one embodiment, the organic acid vehicle is 3% fulvic acid in 97% purified water. Since fulvic acid has less carbon than humic acid, it tends to impart little or no color to the honey. Buffers and/or preservatives may be added to the organic acid vehicle. Colored dyes may also be added. Probiotic bacteria may also be included. In one embodiment, fulvic acid vehicle is supplemented with one of more of the following ingredients: citric acid (or sodium citrate), sodium bicarbonate, brilliant blue dye, lemon yellow dye, one or more, two or more, three or more, four or more probiotic bacteria selected from *Bacillus subtilis, Bacillus pumilus, Bacillus licheniformis, Bacillus megaterium* and *Bacillus laterosporus.* Of course, other probiotic and/or beneficial bacteria may be added. Additional ingredients may also include vitamins, co-factors, minerals, essential oils, micronutrients, sugars, gelatin or other gelling agents, etc. In one embodiment, the formulation includes 4 grams of citric acid and 3.936 grams of sodium bicarbonate, 0.16 grams of brilliant blue and 0.16 grams of lemon yellow, 0.064 grams of *Bacillus subtilis,* 0.064 grams of *Bacillus pumilus,* 0.064 grams of *Bacillus licheniformis,* 0.064 grams of *Bacillus megaterium,* and 0.064 grams of *Bacillus laterosporus* in 2.5 gallons of 3% fulvic acid. The amounts of the dried probiotic bacteria are not particularly limiting. For example, in variations, the amounts of bacteria can range from about 0.01 grams to about 0.2 grams or more, including 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20 grams.

Of course it is understood that in some embodiments, other probiotic and/or other beneficial bacteria or yeast known in the art may be added to the formulation or substituted for these particular microbes. Further other dosages of the microbes may be used. For example, the *Bifidobacterium* and *Lactobacillus* genera (*B. longum, B. breve, B. infantis, L. helveticus, L. rhamnosus, L. plantarum,* and *L. casei*) may be used. *Bifidobacterium bifidum* may help to prevent the formation of various fungal diseases. *Lactobacillus acidophilus* may aid in bee digestion of carbohydrates and stimulate immune response. *Lactobacillus plantarum* may also stimulate the immune system and aid in protein digestion. These microbial additives may be added in dry form about 2, 4, 6, 8, 10, 12, 18, 24, 36 or 72 hours before use to allow a homogeneous and activated additive. The probiotic bacteria hydrate and become active. Preferably, the SUNSHINE Spray is made about 24 hours before use to allow a homogeneous mixture to form.

Next, the fulvic acid mixture is further supplemented with an amalgamated powder comprising nitrogen and various mineral salts, selected from phosphorous, potassium (e.g., potash), and calcium, as well as amino acids are added to the homogeneous mixture. Any salts of the mineral elements may be used. In one embodiment, 2.5 grams of the amalgamated powder is used. The amalgamated powder may include (wt %): 13% of a water-soluble form of nitrogen, 0.1% nitrate salts, 0.2% ammonium salts, 0.24% phosphorous salts, 0.1% potassium salts (potash), 0.4% calcium salts, 3.2% alanine, 5.5% arginine, 5.0% aspartic acid, 10.0% glutamic acid, 18.0% glycine, 0.6% histidine, 2.0% isoleucine, 2.25% lysine, 1.5% phenylalanine, 8.2% proline, 2.2% serine, 1.6% threonine, 1.6% valine, and 0.8% tyrosine; the remainder of the powder consists of nucleic acid fragments, inert ingredients and moisture. The powder is allowed to completely dissolve in the mixture to produce the SUNSHINE Spray supplement.

Methods of Using APICARE™ and SUNSHINE™ Supplements

APICARE Syrup additive is feed to bee colonies diluted in beekeeper's syrup solution. Syrup solutions are typically sugar (sucrose) in water. The standard beekeeper's syrup usually vary from about 1:1 wt/wt sugar to water for Spring feeding, to about 2:1 wt/wt sugar to water for Fall feeding. APICARE Syrup additive may be diluted and mixed at volume ratios of about 1:10, 1:20, 1:30, 1:40, 1:50, 1:60, 1:70, 1:80, 1:90, 1:100, 1:125, 1:150, 1:175, 1:200, 1:300, 1:400, 1:500 and up to about 1:1000 APICARE Syrup additive to beekeeper's syrup. In one embodiment, 1 volume of APICARE Syrup additive is diluted to 100 volumes with beekeeper's syrup. For example, 2.5 gallons of activated APICARE Syrup additive is mixed into 250 gallons of beekeeper's designated syrup solution. After mixing, the homogenous syrup is feed to colonies using bee colony owners' standard feeding schedule. As noted above, such schedule may vary with season. Various feeding techniques can be used, include e.g., (1) using a ¾ gallon inside feeder that replaces one of the interior frames to a standard langstroth 9⅛ deep hive; (2) using a ¾ gallon glass jar that is fitted to be placed inverted on the top of the bee hive; (3) using a plastic bail/bucket that is placed over a hole made into the lid of the beehive; (4) having a large open container that is filled with hay that is then filled with syrup up to just below that hay level; and (5) digging a varying size pit in the ground and lining with plastic then filling with hay and filling with syrup until just below the hay line.

Once activated, APICARE Spray formulation may be applied directly (via aerosol sprayer, liquid sprayer, etc.) to the main brood nest of the colony. Dosages may vary depending on the heath of the colony. Routine prophylactic application may use about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 liquid oz. In some embodiments, about 1.5 oz is sprayed directly onto the brood nest. The spray application may occur about one time every 6, 8, 10, 12, 14, 16, 18, 20, 22, 24, 26, 28 or 30 days. In one embodiment, the spray is applied about every 15-17 days.

EXAMPLE 1

Treatment of *Nosema*

APICARE Syrup additive is made by mixing 1.134 Kg humic acid with 9.462 liter of reverse osmosis filtered water. The diluted humic acid vehicle is blended for about 30-60 minutes in a sterile container at room temperature until clear. To the vehicle is added 4 grams of citric acid and 3.936 grams of sodium bicarbonate, 0.16 grams of brilliant blue and 0.16 grams of lemon yellow, 0.064 grams of *Bacillus subtilis*, 0.064 grams of *Bacillus pumilus*, 0.064 grams of *Bacillus licheniformis*, 0.064 grams of *Bacillus megaterium*, and 0.064 grams of *Bacillus laterosporus*. The mixture is incubated with gentle stirring for 24 hours at room temperature, thereby allowing the probiotic bacteria to hydrate and activate.

About 2.5 gallons of activated APICARE Syrup additive is mixed into 250 gallons of beekeeper's syrup solution (e.g., 1:1 sugar to water by weight). After mixing, the homogenous syrup is fed to colonies as described above. Before feeding with APICARE Syrup additive, symptoms of *Nosema*, including dysentery and crawling are observed, especially in the female worker bees after a period of wet weather in April. Yellow stripes are also seen both in and outside of the hive.

After feeding as above for 4-21 days or more, the visible symptoms of *Nosema* are disappearing from the hive. By 3-6 weeks, the hive appears to be healthy and free of *Nosema* symptoms. A second feeding was undertaken in September.

EXAMPLE 2

Treatment of American Foulbrood

American foulbrood infection is diagnosed in colonies after observing darkened/dead larvae in sealed cells in the bee brood. APICARE Syrup additive is made and fed to the colonies as described in Example 1.

After feeding as above for 7-21 days, the visible symptoms of American Foulbrood are disappearing from the hive. By 3-6 weeks, the hive appears to be healthy and free of American Foulbrood symptoms. A second feeding was undertaken in September.

EXAMPLE 3

Treatment of Viral Pathogens

Infection with a virus that causes sacbrood is diagnosed in the main brood nest of the colony after observing elevated numbers of punctured cell caps. APICARE Spray is prepared by mixing about 0.085 Kg of humic acid in about 9.462 liters of distilled water. To the dilute acid is added 4 grams of citric acid and 3.936 grams of sodium bicarbonate, 0.16 grams of brilliant blue and 0.16 grams of lemon yellow, 0.064 grams of *Bacillus subtilis*, 0.064 grams of *Bacillus pumilus*, 0.064 grams of *Bacillus licheniformis*, 0.064 grams of *Bacillus megaterium*, and 0.064 grams of *Bacillus laterosporus*. The APICARE Spray formulation is incubated with gentle mixing for 24 hours at room temperature before use.

About 1.5 fluid oz of the activated APICARE Spray is applied directly to the top bars of the main brood nest of the colony by aerosol sprayer. The dosing continues for 15 days, one application per day. After spray application for 15 days, the visible symptoms of sacbrood are disappearing from the hive. By 3-6 weeks, the hive appears to be healthy and free of sacbrood infection. A second feeding was undertaken in September.

EXAMPLE 4

Prophylaxis and Promotion of General Colony Health Using APICARE

APICARE Syrup additive is made and fed to healthy colonies in the Spring as described in Example 1. The colonies appear vibrant, healthy and free of any visible signs of *Nosema*, American Foulbrood and sacbrood throughout the Spring and Summer seasons.

EXAMPLE 5

Prophylaxis and Promotion of General Colony Health Using SUNSHINE

SUNSHINE Spray formulation is made by mixing 4 grams of citric acid and 3.936 grams of sodium bicarbonate, 0.16 grams of brilliant blue and 0.16 grams of lemon yellow, 0.064 grams of *Bacillus subtilis*, 0.064 grams of *Bacillus pumilus*, 0.064 grams of *Bacillus licheniformis*, 0.064 grams of *Bacillus megaterium*, and 0.064 grams of *Bacillus laterosporus* into 2.5 gallons of 3% fulvic acid/97% purified water. After allowing the mixture to rest for 24 hours, a homogeneous mixture was observed and the bacteria were activated.

Next 2.5 grams of an amalgamated powder supplement was added to the mixture. The amalgamated powder supplement included: 13% of water-soluble nitrogen, 0.1% nitrate salts, 0.2% ammonium salts, 0.24% phosphorous salts, 0.1% potassium salts (potash), 0.4% calcium salts, 3.2% alanine, 5.5% arginine, 5.0% aspartic acid, 10.0% glutamic acid, 18.0% glycine, 0.6% histidine, 2.0% isoleucine, 2.25% lysine, 1.5% phenylalanine, 8.2% proline, 2.2% serine, 1.6% threonine, 1.6% valine, and 0.8% tyrosine; the remainder of the powder consists of nucleic acid fragments, inert ingredients and moisture.

After the powder supplement had dissolved in the 3% fulvic acid mixture, 1.5 oz of the SUNSHINE Spray formulation was sprayed on the top bars of the main brood cluster once a day for 15-17 days. The colonies appear vibrant, healthy and free of any visible signs of *Nosema*, American Foulbrood and sacbrood throughout the Spring and Summer seasons.

EXAMPLE 6

Prophylaxis and Treatment of *Varroa* mites

APICARE Syrup additive is made and fed to healthy colonies in April and September as described in Example 1. Analyses of *Varroa* mite counts per 100 bees in the 8 tested hives is shown in Table 1 and compared with composite monthly national average (NHBS) and previous year's national average (Tier 4 2014).

The data for *Varroa* presented in Table 1 was independently generated by the Bee Informed Partnership (beeinformed.org) in association with the USDA. The report further stated that greater than or equal to 5 mites per 100 bees was considered as approaching a high threshold at or beyond which the beekeeper may want to consider some *Varroa* mite control strategy. The data cover the time period from Summer into Fall, when mite counts tend to increase sharply. The results indicate that hives fed APICARE Syrup additive as described in Example 1 provide unexpected and dramatic resistance to mite infestation compared to the national averages, with *Varroa* mite counts well below the threshold.

TABLE 1

*Varroa* (mites per 100 bees)
Beekeeper: T415-AACK Year: 2015 Report date: 09/18/15

| TEST HIVES | JULY | AUGUST | SEPTEMBER |
|---|---|---|---|
| 1 | 0.0 | 0.7 | 1.0 |
| 2 | 0.0 | 0.0 | 2.8 |
| 3 | 0.0 | 0.0 | 2.5 |
| 4 | 0.0 | 0.7 | 3.0 |
| 5 | 0.0 | 0.6 | 0.0 |
| 6 | 0.0 | 0.5 | 0.0 |
| 7 | 0.0 | 0.0 | 1.6 |
| 8 | 0.0 | 0.0 | 1.7 |
| Monthly Average (Test Hives) | 0.0 ± 0.0* (8) | 0.31 ± 0.28 (8) | 1.58 ± 0.99 (8) |
| NHBS Monthly Average** | 3.4 ± 0.43 (335) | 3.99 ± 0.34 (470) | 6.13 ± 0.53 (597) |
| Tier 4 2014 Monthly Average§ | 2.9 ± 0.45 (296) | 4.86 ± 0.78 (277) | 6.64 ± 1.11 (223) |

*Data presented: average ± 95% Confidence Interval (# of samples).
**National Honey Bee Survey (NHBS) is a national effort sponsored by USDA Animal and Plant Health Inspection Service (APHIS) in collaboration with the Agricultural Research Service (ARS) and University of Maryland (UMD). To date, the data provided for the APHIS monthly average is a composite of data from 2009-Present.
§Tier 4 (Real Time Disease Load Survey) 2014 Monthly Average includes Tier 4 data starting in June 2013.

EXAMPLE 7

Prophylaxis and Treatment of *Nosema*

APICARE Syrup additive is made and fed to healthy colonies in April and September as described in Example 1. Analyses of *Nosema* counts (million spores per bee) in 8 tested hives is shown in Table 2 and compared with composite monthly national average (NHBS) and previous year's national average (Tier 4 2014).

TABLE 2

*Nosema* (millions of spores per bee)
Beekeeper: T415-AACK Year: 2015 Report date: 09/18/15

| TEST HIVES | JULY | AUGUST | SEPTEMBER |
|---|---|---|---|
| 1 | 0.2 | 0.0 | 0.0 |
| 2 | 0.2 | 0.0 | 0.4 |
| 3 | 1.4 | 0.2 | 0.0 |
| 4 | 0.1 | 0.3 | 0.0 |
| 5 | 1.5 | 0.1 | 0.8 |
| 6 | 1.0 | 0.0 | 0.5 |
| 7 | 0.8 | 0.0 | 0.6 |
| 8 | 1.6 | 0.2 | 0.5 |
| Monthly Average (Test Hives) | 0.84 ± 0.52* (8) | 0.09 ± 0.09 (8) | 0.33 ± 0.25 (8) |
| NHBS Monthly Average** | 0.37 ± 0.09 (335) | 0.17 ± 0.05 (468) | 0.12 ± 0.03 (596) |
| Tier 4 2014 Monthly Average§ | 2.9 ± 0.45 (296) | 4.86 ± 0.78 (277) | 6.64 ± 1.11 (223) |

*Data presented: average ± 95% Confidence Interval (# of samples).
**National Honey Bee Survey (NHBS) is a national effort sponsored by USDA Animal and Plant Health Inspection Service (APHIS) in collaboration with the Agricultural Research Service (ARS) and University of Maryland (UMD). To date, the data provided for the APHIS monthly average is a composite of data from 2009-Present.
§Tier 4 (Real Time Disease Load Survey) 2014 Monthly Average includes Tier 4 data starting in June 2013.

The data for *Nosema* presented in Table 2 was independently generated by the Bee Informed Partnership (beeinformed.org) in association with the USDA. The report further stated that greater than or equal to one million spores per bee was considered to be an acceptable threshold. The data cover the time period from Summer into Fall, when mite counts are typically dropping. The results indicate that hives fed APICARE Syrup additive as described in Example 1 (feeding management—in April and September) provide unexpected reduction in levels of *Nosema* infection compared to the national averages (particularly compared to the previous year's numbers), with *Nosema* spore counts largely below the threshold.

What is claimed is:

1. A formulation for promoting honeybee health, the formulation comprising:
    an aqueous solution comprising an organic acid, wherein the organic acid comprises humic acid at 0.1 to 10 Kg humic acid per 10 liters total volume;
    one or more buffering agents, wherein the one or more buffering agents are citric acid and sodium bicarbonate;
    one or more coloring dyes;
    *Bacillus subtilis;*
    *Bacillus pumilus;*
    *Bacillus licheniformis;*
    *Bacillus megaterium;* and
    *Bacillus laterosporus,*
    wherein the formulation further comprises nitrogen, phosphate, potassium, calcium, and one or more amino acids selected from the group consisting of alanine, arginine, aspartic acid, glutamic acid, glycine, histidine, isoleucine, lysine, phenylalanine, proline, serine, threonine, valine, and tyrosine, and
    wherein promoting honeybee health comprises increasing resistance to mite infestation and reducing levels of *Nosema* infection.

2. The formulation of claim 1, wherein the aqueous solution comprises 1.134 Kg humic acid per 10 liters total volume.

3. The formulation of claim 1, wherein the aqueous solution comprises 4 grams of citric acid and 4 grams of sodium bicarbonate per 10 liters total volume.

4. The formulation of claim 1, wherein the one or more coloring dyes are selected from the group consisting of brilliant blue and lemon yellow.

5. The formulation of claim 4, wherein the aqueous solution comprises 0.16 grams of brilliant blue and 0.16 grams of lemon yellow per 10 liters total volume.

6. The formulation of claim 1, wherein the aqueous solution comprises 0.064 grams of dried culture of each of *Bacillus subtilis, Bacillus pumilus, Bacillus licheniformis, Bacillus megaterium,* and *Bacillus laterosporus* per 10 liters total volume.

7. The formulation of claim 1, wherein the formulation is in the form of a syrup additive or a spray.

8. The formulation of claim 1, wherein the formulation further comprises additional active ingredients, inert ingredients, or both.

9. A kit for making the formulation of claim 1, the kit comprising humic acid, citric acid and sodium bicarbonate, brilliant blue and lemon yellow dyes, and a dried probiotic culture mix, comprising *bacillus subtilis, bacillus pumilus, bacillus licheniformis, bacillus megaterium,* and *bacillus laterosporus.*

10. The kit of claim 9, wherein the ingredients are pre-weighed and packaged in sterile disposable bags sufficient for mixing 10 liters of formulation.

11. The kit of claim 9, further comprising instructions for mixing, activating and using the formulation.

12. A method of treating a honeybee infection, comprising mixing the formulation of claim 1 and administering the formulation to a honeybee colony in need thereof, wherein the honeybee infection comprises mite infestation and *Nosema* infection.

13. The method of claim 12, wherein administering comprises feeding the formulation in a 1:1 to 1:2 mixture of formulation to beekeeper's syrup solution.

14. The method of claim 12, wherein administering comprises spraying the formulation directly onto a brood nest of the colony.

* * * * *